United States Patent
Sniffin et al.

(10) Patent No.: US 10,045,830 B2
(45) Date of Patent: Aug. 14, 2018

(54) STORAGE DEVICE FOR MEDICAL COMPONENTS AND METHOD OF USE

(71) Applicant: Covidien LP, Mansfield, MA (US)

(72) Inventors: Kevin Sniffin, Roxbury, CT (US); Divya Vijaya Vittala Nadig, Hamden, CT (US)

(73) Assignee: Covidien LP, Mansfield, MA (US)

( * ) Notice: Subject to any disclaimer, the term of this patent is extended or adjusted under 35 U.S.C. 154(b) by 33 days.

(21) Appl. No.: 15/072,500

(22) Filed: Mar. 17, 2016

(65) Prior Publication Data

US 2016/0310225 A1    Oct. 27, 2016

Related U.S. Application Data

(60) Provisional application No. 62/151,459, filed on Apr. 23, 2015.

(51) Int. Cl.
*A61B 50/22* (2016.01)
*A61B 50/20* (2016.01)
*A61B 50/30* (2016.01)
*A61B 17/068* (2006.01)

(52) U.S. Cl.
CPC .............. *A61B 50/22* (2016.02); *A61B 50/20* (2016.02); *A61B 50/30* (2016.02); *A61B 2017/0688* (2013.01)

(58) Field of Classification Search
CPC ...... F16M 13/00; F16M 11/22; F16M 11/041; F16M 13/02; F16M 13/022; Y10T 24/155; Y10T 24/1498; Y10T 279/3443; A61L 350/22; A61B 50/22; A61B 50/20; A61B 50/30; A61B 2017/0688

USPC .................................................. 211/85.13
See application file for complete search history.

(56) References Cited

U.S. PATENT DOCUMENTS

| | | | |
|---|---|---|---|
| 1,913,105 A * | 6/1933 | Case | A47L 13/512 206/362 |
| 2,224,027 A * | 12/1940 | Tate | G09F 5/042 206/476 |
| 2,472,028 A | 5/1949 | Son | |
| 4,008,802 A | 2/1977 | Freitag | |
| 4,023,678 A | 5/1977 | Fiedler | |
| 4,074,397 A * | 2/1978 | Rosin | A61M 25/02 128/DIG. 15 |
| 4,167,230 A | 9/1979 | Barratt | |
| 4,193,588 A * | 3/1980 | Doneaux | A61J 11/00 269/287 |
| 4,243,140 A | 1/1981 | Thrun | |
| 4,321,999 A | 3/1982 | Higgins | |

(Continued)

OTHER PUBLICATIONS

European Search Report EP16166601 dated Aug. 8, 2016.

*Primary Examiner* — Ko H Chan (57) ABSTRACT

A storage device is provided to store a tool or component in an operating theater and includes a receiving portion and a retaining member. The receiving portion is configured to support the tool or component thereon. The retaining member is transitionable between an initial configuration and a deployed configuration and includes a securing region thereon. In the deployed configuration, the retaining member is spaced away from a plane defined by a surface of the receiving portion. The securing region is configured to facilitate the passage of a tool or component through the retaining member such that the tool or component is secured therein.

19 Claims, 6 Drawing Sheets

(56) References Cited

U.S. PATENT DOCUMENTS

| | | | |
|---|---|---|---|
| 4,490,141 A * | 12/1984 | Lacko | A61M 25/02 128/879 |
| 4,512,466 A * | 4/1985 | Delang | A61B 50/20 206/370 |
| 4,591,048 A | 5/1986 | Eldridge, Jr. | |
| 4,596,329 A | 6/1986 | Eldridge, Jr. | |
| 4,597,493 A * | 7/1986 | Bruso | B65D 73/0021 206/363 |
| 4,631,783 A * | 12/1986 | Hayashi | F16M 13/00 211/70.6 |
| 4,637,513 A | 1/1987 | Eldrige, Jr. | |
| 4,644,610 A * | 2/1987 | Fish | A01G 13/04 211/70.6 |
| 4,762,688 A | 8/1988 | Berry, Jr. | |
| 4,962,757 A * | 10/1990 | Stefan | A61M 25/02 128/DIG. 26 |
| 5,024,326 A | 6/1991 | Sandel et al. | |
| 5,221,265 A * | 6/1993 | List | A61M 25/02 128/DIG. 26 |
| 5,234,106 A * | 8/1993 | Transue | B65D 73/0021 206/349 |
| 5,301,871 A * | 4/1994 | Gross | A47G 19/065 206/562 |
| 5,316,142 A | 5/1994 | Jain | |
| 5,353,974 A | 10/1994 | Maurizio | |
| 5,389,082 A | 2/1995 | Baugues et al. | |
| 5,402,971 A * | 4/1995 | Bower | F16L 3/233 24/16 PB |
| 5,699,909 A | 12/1997 | Foster | |
| 5,715,942 A | 2/1998 | Li et al. | |
| 5,799,788 A | 9/1998 | Webb | |
| 6,138,278 A * | 10/2000 | Taylor | A41D 13/1227 2/114 |
| 6,161,263 A * | 12/2000 | Anderson | A41B 11/002 24/30.5 S |
| 6,215,052 B1 * | 4/2001 | Giddens | G10D 3/163 211/120 |
| 6,234,327 B1 | 5/2001 | Reed | |
| 6,854,598 B2 | 2/2005 | Koseki | |
| 6,930,244 B1 * | 8/2005 | Nebel | B60R 16/0207 174/486 |
| 7,070,051 B2 | 7/2006 | Kanner et al. | |
| 7,497,330 B2 | 3/2009 | Anthony et al. | |
| 8,418,851 B2 | 4/2013 | Culligan et al. | |
| 9,307,982 B2 | 4/2016 | Gorek et al. | |
| 2003/0155259 A1 | 8/2003 | Koseki | |
| 2004/0129591 A1 | 7/2004 | Koseki | |
| 2005/0103949 A1 | 5/2005 | Ross et al. | |
| 2005/0269228 A1 | 12/2005 | Kanner et al. | |
| 2008/0091221 A1 | 4/2008 | Brubaker et al. | |
| 2008/0166682 A1 | 7/2008 | Bjorn et al. | |
| 2012/0199704 A1 | 8/2012 | Taylor | |

* cited by examiner

STORAGE DEVICE FOR MEDICAL COMPONENTS AND METHOD OF USE

CROSS-REFERENCE TO RELATED APPLICATIONS

This application claims the benefit of and priority to U.S. Provisional Patent Application No. 62/151,459 filed Apr. 23, 2015, the entire disclosure of which is incorporated by reference herein.

TECHNICAL FIELD

The present disclosure relates to a storage device, and more specifically to a storage device for medical components utilized in an operating theater.

BACKGROUND

Various types of surgical devices are used for performing medical procedures on organs, tissues, and/or vessels. In many cases, the medical procedure involves inserting surgical tools, devices, or components thereof, into the body of a patient through a natural orifice or an incision. Surgical tools inserted into the body may be removed prior to the completion of the medical procedure, or may be designed to remain within the body. In cases where the surgical tools, and components thereof, are intended to be removed from the patient, an accounting of all components must be rigorously performed to ensure nothing is left inside the body. Surgical tools or components unintentionally left in the body require additional surgical procedures for removal. Additionally, as tools and components are used, replaced, interchanged, or reloaded, contaminated tools or components quickly litter the operating theater. These used tools or components typically retain biological waste thereon, such as, for example, blood or bodily fluids, and must be contained in a manner to avoid contamination with sterile equipment or the surrounding environment.

Accordingly, it is highly desirable for an operator to easily and efficiently account for the quantity of tools or components introduced into the operating theater, retain introduced tools or components before or after use, and verify prior to closing an incision or completing the medical procedure that all introduced tools or components are accounted for. Additionally, when using tools with interchangeable or reloadable components, there is a further desire to maintain an accurate count of the new and/or used components, to ensure that a used component is not re-inserted into the body unintentionally. A further desire is to retain and account for any tools or components that may have broken during use, to ensure that a broken component is not re-inserted into the body unintentionally.

SUMMARY

The present disclosure relates to a storage device for medical components utilized in an operating theater. The storage device includes a receiving portion adapted to support a component and a retaining member coupled to the receiving portion. The retaining member is transitionable between an initial configuration and a deployed configuration, and includes at least one securing region. The at least one securing region is circumscribed by material of the retaining member. In the deployed configuration, the retaining member is spaced away from a plane defined by a surface of the receiving portion. The at least one securing region of the retaining member is configured to receive a component therein.

In an embodiment, the retaining member and the surface of the receiving portion are coplanar in the initial configuration. The receiving portion may further include a raised lip extending along an outer perimeter. The at least one securing region may further define a perforated pattern. The storage device may further include an attachment member coupled at a first end to the receiving portion. The attachment member has a second end configured to temporarily affix to a receiving slot disposed on the receiving portion. The storage device may further include a plurality of retaining members, where each retaining member of the plurality of retaining members is independently transitionable between the initial and deployed configurations. The receiving portion of the storage device may further include an absorbent area. The receiving portion may further include a perimeter configured to increase frictional resistance, such that the component is frictionally inhibited from escaping the receiving portion. The retaining member may further be configured to be temporarily fixed in the initial configuration and biased into the deployed configuration. Once the retaining member is released from the initial configuration, the retaining member assumes the deployed configuration. The at least one securing region of the retaining member may be configured to receive a component such as a reloadable staple cartridge, a reloadable tack cartridge, a removable end effector, and a surgical mesh.

In another embodiment, the storage device includes a receiving portion adapted to support a component, a retaining member coupled to the receiving portion, and an attachment member. The retaining member is transitionable between an initial configuration and a deployed configuration, and includes a plurality of securing regions. The attachment member is coupled at a first end to the receiving portion and has a second end configured to temporarily affix to a receiving slot disposed on the receiving portion. In the initial configuration the retaining member is coplanar with the receiving portion, and in the deployed configuration the retaining member is spaced away from a plane defined by a surface of the receiving portion. A component is insertable through each of the securing regions of the plurality of securing regions of the retaining member. Each securing region of the plurality of securing regions is further configured to exert a compressive force upon an outer surface of the component such that the component is secured to the storage device. In another embodiment, a kit is provided. The kit includes a storage device and a component. The storage device includes a receiving portion and a retaining member coupled to the receiving portion. The retaining member is transitionable between an initial configuration and a deployed configuration, and includes a securing region. The securing region is defined by a contiguous outer surface. In the deployed configuration, the retaining member is spaced away from a plane defined by a surface of the receiving portion. A component is insertable into the securing region. The kit may further include a tool. The tool may be a surgical stapler, a surgical tack applier, a reloadable fixation device, a vessel sealer, an ablation probe, an endoscopic instrument, and a retractor. The component may be a reloadable staple cartridge, a reloadable tack cartridge, a removable end effector, and a surgical mesh. The storage device may further include an attachment member coupled at a first end to the receiving portion and have a second end configured to temporarily affix to a receiving slot on the receiving portion. The attachment member may temporarily secure the storage device to the component or the tool.

In another embodiment, a method of storing a tool or component is provided. The method includes transitioning a retaining member of a storage device from an initial configuration into a deployed configuration. In the deployed configuration the retaining member is spaced away from a plane defined by a surface of a receiving portion of the storage device. The method further includes approximating a component to a securing region of the retaining member, where the securing region defines a perforated pattern, and inserting the component through the securing region and through a thickness of the retaining member, such that the component is affixed thereto. The method may further include separating the storage device from a tool. The storage device may be attached to the tool with an attachment member. The method may additionally include providing the storage device in the initial configuration, where the retaining member and the receiving portion are coplanar in the initial configuration.

BRIEF DESCRIPTION OF THE DRAWINGS

The foregoing and other features of the present disclosure will become apparent to one skilled in the art to which the present disclosure relates upon consideration of the following description of the disclosure with reference to the accompanying drawings, wherein.

DETAILED DESCRIPTION

Embodiments of the present disclosure will now be described in detail with reference to the drawings, in which like reference numerals designate identical or corresponding elements in each of the several views. In the following description, well-known functions or constructions are not described in detail to avoid obscuring the present disclosure in unnecessary detail.

Figure 1A:
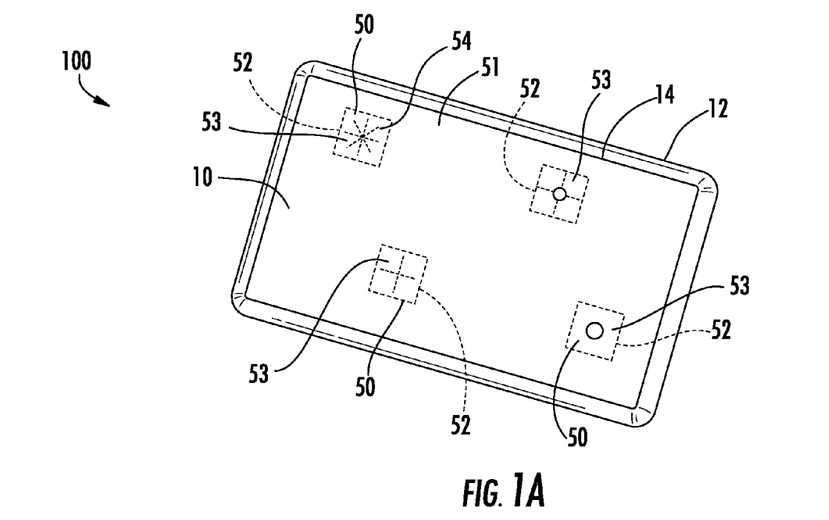
FIG. 1A is a front perspective view of a storage device in accordance with an embodiment of the present disclosure, with retaining members in an initial configuration.
Figure 1B:
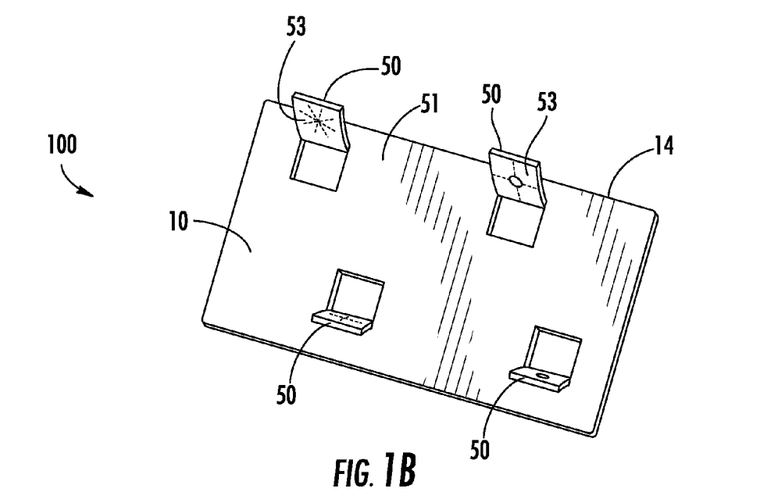
FIG. 1B is a front perspective view of the storage device of FIG. 1A with the retaining members in a deployed configuration.

With reference to FIGS. 1A and 1B, an embodiment of a storage device in accordance with the present disclosure is shown generally as storage device 100. It is envisioned that storage device 100 may be used to hold, secure, or retain tools, and/or components thereof, at a localized position, such as, for example, a table, tray, or cart. Storage device 100 additionally serves as a visual cue to an operator such that an accurate accounting of used tools or components can be maintained to ensure that all tools and components introduced during a surgical procedure are collected prior to completing the surgical procedure. In this manner, a tool or component can be easily localized in a desired area within the operating theater, the tool or component can remain at the desired location without any unwanted movement, such as, for example, rolling off a table or sliding around in a tray, and further, the possibility of unintentionally leaving the tool or component within the body of the patient can be reduced.

Storage device 100 may come in a variety of sizes and configuration, as discussed below, such that a number of tools and components may be retained therein. Solely for example, and not intended to be limiting, storage device 100 may be configured to retain such tools as, surgical staplers, tack appliers, reloadable fixation devices, vessel sealers, ablation probes, endoscopic instruments, trocars, biopsy needles, catheters, instrument coupling tools and corresponding fittings, or any other surgical device. Storage device 100 may additionally or alternatively be configured to retain such components as, for example, reloadable staple cartridges, reloadable tack cartridges, removable or interchangeable end effectors, surgical meshes, hypotubes, syringes, and any other surgical components. For the purposes of clarity, and for the sake of brevity, storage device 100 will be described herein with reference to a surgical stapler and counterpart components thereof, such as, a staple cartridge used with a reloadable surgical stapler. Storage device 100 additionally provides a localized position to retain any discarded tools or components, such as, for example, depleted reload cartridges, expended single use tools, or broken or defective tools, such that the tool or component is not reintroduced into the patient unintentionally. As staple cartridges are depleted and eventually replaced with a new staple cartridge, the depleted staple cartridges may be placed within storage device 100 such that depleted staple cartridges are kept at a localized position and the operator may visually assess the quantity of depleted staple cartridges, and thus more easily prevent a depleted staple cartridge from being reloaded into the stapler.

Storage device 100 defines a surface or receiving portion 10 configured to support the tool or component thereon and includes one or more retaining members 50. Each retaining member 50 is configured to permit the tool or component to pass through a thickness thereof (FIG. 3B), thereby affixing the tool or component to receiving portion 10 and storage device 100. Retaining members 50 may further provide visual indicia as to the quantity of tools and components which were used during the particular procedure. As retaining member 50 is transitioned into a deployed configuration to receive an individual tool or component, the position of retaining member 50 is altered, as discussed below, which serves as a visual indication that a tool or component is retained therein. It is envisioned that as spent staple cartridges are affixed to retaining members 50, the operator can quickly and easily maintain an accurate and updated count of the spent and depleted staple cartridges used during the procedure. By affixing depleted staple cartridges to storage device 100, the operator may further account for the discarded staple cartridges to better assess if any staple cartridges are unaccounted for.

As referenced above, retaining member 50 is transitionable between an initial configuration and the deployed configuration. In the initial configuration retaining member 50 is approximated to a surface 51 of receiving portion 10 such that a low profile is maintained and storage device 100 may be easy packaged in a compact and space saving fashion. In the deployed configuration, retaining member 50 is spaced away from a plane defined by the surface 51 of receiving portion 10 such that the surgical tool or component may be easily affixed thereto. Retaining member 50 may be substantially flush or coplanar with the surface 51 of receiving portion 10 in the initial configuration (FIG. 1A), and may protrude or extend from the surface 51 of receiving portion 10 in the deployed configuration (FIG. 1B). It is contemplated that in the initial configuration, the coplanar relationship of retaining member 50 and receiving portion 10 provides storage device 100 with a minimal height. The minimal height of storage device 100 facilitates the efficient packaging thereof, such that a modest amount of surface area or space within the operating theater is used by one or more storage devices 100. Retaining member 50 may be transitioned from the initial configuration into the deployed configuration by physically deforming retaining member 50, such as, for example, by bending, folding, or re-contouring the shape of retaining member 50. Retaining member 50 may additionally, or alternatively, be transitioned by using an instrument, such as the tool or component being inserted therein, to pry or pull retaining member 50 from the initial configuration into the deployed configuration. It is contemplated that with retaining member 50 in the initial configuration, the tool or component can be inserted therein to create a mechanical advantage, such that the tool or component can be used to pry or pull the retaining member 50 into the deployed configuration. It is envisioned that retaining member 50 may be maintained in the deployed configuration by any known means in the art, such as, for example, construction of storage device 100 from a deformable material, integration of a mechanical interlock mechanism between the retaining member 50 and receiving portion 10, such as a snap-fit, latch, or clasp, inclusion of an adhesive portion or strip disposed between the retaining member 50 and receiving portion 10, incorporation of a biasing member disposed between the retaining member 50 and receiving portion 10, construction of storage device 100 such that retaining member 50 is biased into the deployed configuration, or any combination thereof.

As illustrated in FIGS. 1A and 1B, it is envisioned that substantially all of the boundary between receiving portion 10 and retaining member 50 may be defined by a pre-cut or perforated section 52 (shown in phantom). Perforated section 52 may define three out of the four sides of retaining member 50, such that as retaining member 50 is physically deformed, the three sides of perforated section 52 rip or tear, and retaining member 50 is folded along the fourth side which is still connected to receiving portion 10. Retaining member 50 may be folded along the fourth side to reposition the retaining member 50 to extend in a direction away from receiving portion 10, facilitating fixation of surgical tools or components thereto. It should be appreciated that while retaining member 50 is generally shown as a square cutout of receiving portion 10, it is envisioned that retaining member 50 may assume any suitable shape, such as, for example, a circle, a triangle, a trapezoid, or a semi-circle.

Figure 2:
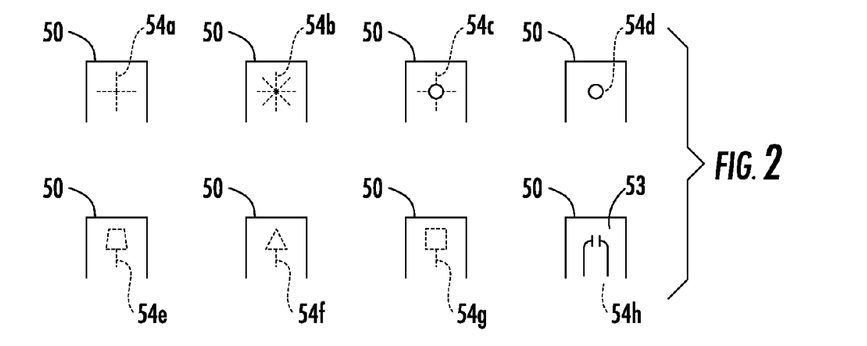
FIG. 2 is a front view of a variety of perforated configurations of the storage device of FIG. 1 in accordance with the present disclosure.

Retaining member 50 further includes a securing region 53 disposed on the opposing major surfaces of retaining member 50, such that the thickness (not shown) of retaining member 50 is defined therebetween. It is contemplated that securing region 53 may be disposed on retaining member 50 such that an unbroken or solid boundary is created between securing region 53 and an outer perimeter of retaining member 50. In other words, securing region 53 is circumscribed by the material that forms the retaining member 50 or is defined by a contiguous or uninterrupted outer surface. Such a boundary may serve to increase the strength and resilience of securing region 53, such that a tool or component inserted therein is inhibited from tearing through, or ripping out of, retaining member 50. Securing region 53 defines a weakened or deformable portion of retaining member 50 which may be pre-cut or perforated, such that a tool or component "C" may be inserted therethrough, as seen in FIG. 3B. It is envisioned that securing region 53 may have different pre-cut or perforated pattern or configurations, such as, for example, the illustrated perforated configurations 54a-h as shown in phantom in FIG. 2. It should be appreciated that securing region 53 may define any suitable perforated configuration, whereas FIG. 2 is merely exemplary in nature. Perforated configurations 54a-h may extend through substantially all of the thickness of retaining member 50, and allows the tool or component to more easily penetrate though the thickness of retaining member 50. As storage device 100 may include one or more retaining members 50 each having a securing region 53 thereon, the individual securing regions 53 may define the same, or a unique, perforated configuration 54a-h. As should be appreciated, the perforated configuration 54a-h may correspond to a particular tool or component, and/or may be a general configuration to accommodate a wide range of possible tool or component shapes and sizes.

Prior to the insertion of the component "C" through securing region 53, securing region 53 maintains a closed configuration (FIG. 3A), where securing region 53 may be substantially flush or coplanar with the surface of retaining member 50. It is envisioned that securing region 53 may be biased into the closed configuration, such that the bias must be overcome to pierce, puncture, or push the component "C" therethrough. As a result, any tool or component which passes through securing region 53 encounters a compressive force along their outer surface as the bias of the securing region 53 acts to return it to the closed configuration.

Figure 3A:
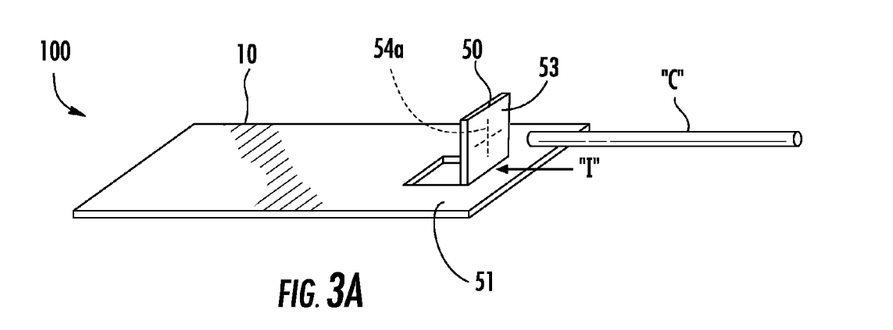
FIG. 3A is a side perspective view of the storage device of FIG. 1, with the retaining member transitioned into the deployed configuration and including a component.
Figure 3B:
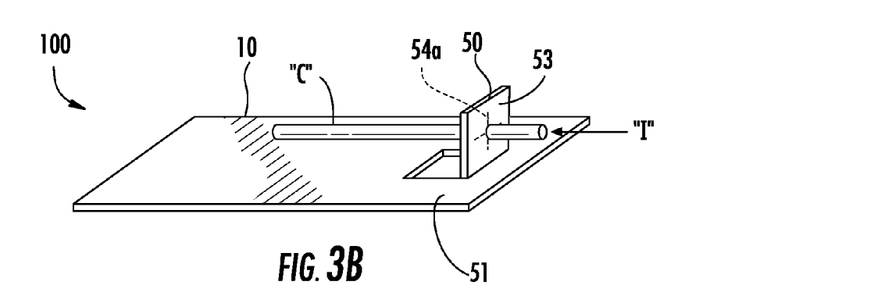
FIG. 3B is a side perspective view of the storage device of FIG. 3A, with the retaining member in the deployed configuration and the component disposed therein.

With reference to FIG. 3A, as an end of component "C" is brought into abutment with the securing region 53 of retaining member 50, the instrument is placed into approximation with the perforated configuration 54a-h. As the component is forcibly inserted through the retaining member 50 in the direction of arrow "I", the retaining member 50 is facilitated by securing region 53 to secure and retain component "C" therein. More particularly, as component "C" is pushed through the securing region 53 and the thickness of retaining member 50, securing region 53 frictionally engages with, and/or exerts a compressive force on, the outer surface of component "C", thereby securing component "C" in retaining member 50.

It is further contemplated that securing region 53, and/or perforated configuration 54a-h, may be configured to permit uni-directional insertion. In such an embodiment, component "C" may only be inserted through securing region 53 in the direction "I", such that a major portion of component "C" which extends from securing region 53 is positioned over receiving portion 10, the benefits of which are discussed herein below with respect to receiving portion 10 and the retention of the tool, component, and/or biological waste thereon. It is further envisioned that securing region 53 may be configured to allow uni-directional translation of component "C" through retaining member 50. Once component "C" is inserted through securing region 53 in the direction of arrow "I" (FIG. 3B), component "C" cannot be pulled, or backed out, in the opposite direction of arrow "I".

Storage device 100 may further include a raised edge, ridge, or lip 12 extending from an outer perimeter 14 of the receiving portions 10. Lip 12 is configured to prevent tools, components, and/or biological waste from unintentionally leaving receiving portion 10. Lip 12 may alternatively or additionally include a textured surface, such that a high friction perimeter is created around receiving portion 10 to further prevent the tools or components from leaving receiving portion 10. It is further contemplated that substantially all, or a part of, receiving portion 10 may include a textured, tacky, or adhesive surface to facilitate the retention of tools or components thereon. It should be appreciated that while lip 12 has been described and illustrated with respect to storage device 100, lip 12 may be utilized in a similar fashion with any of the storage devices disclosed herein.

Figure 4A:
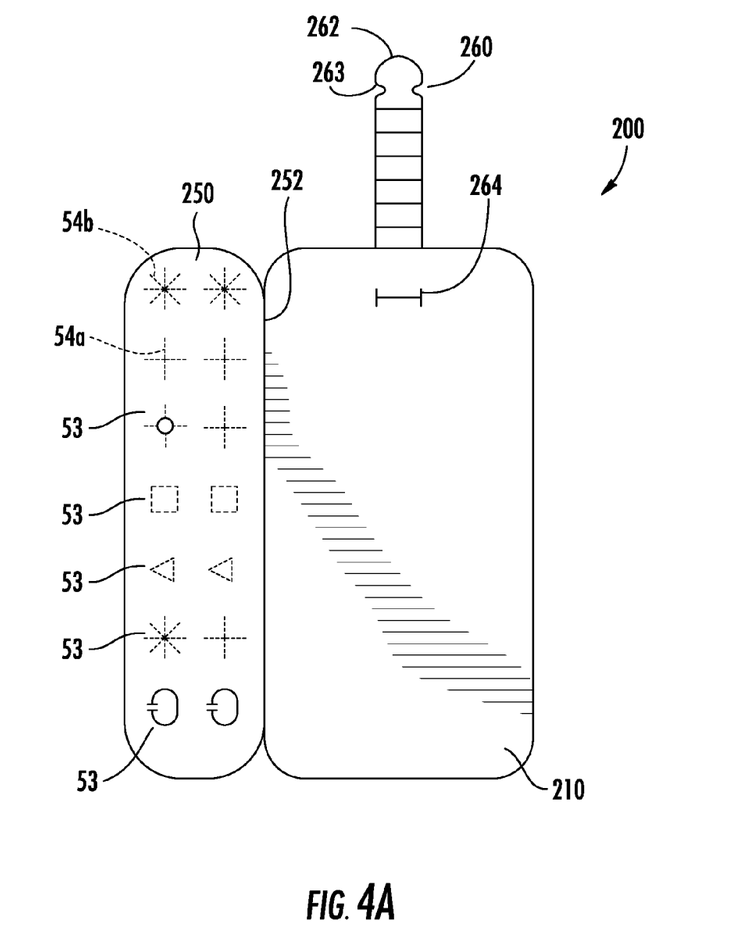
FIG. 4A is a top view of a storage device in accordance with another embodiment of the present disclosure, with a retaining member in an initial configuration.
Figure 4B:
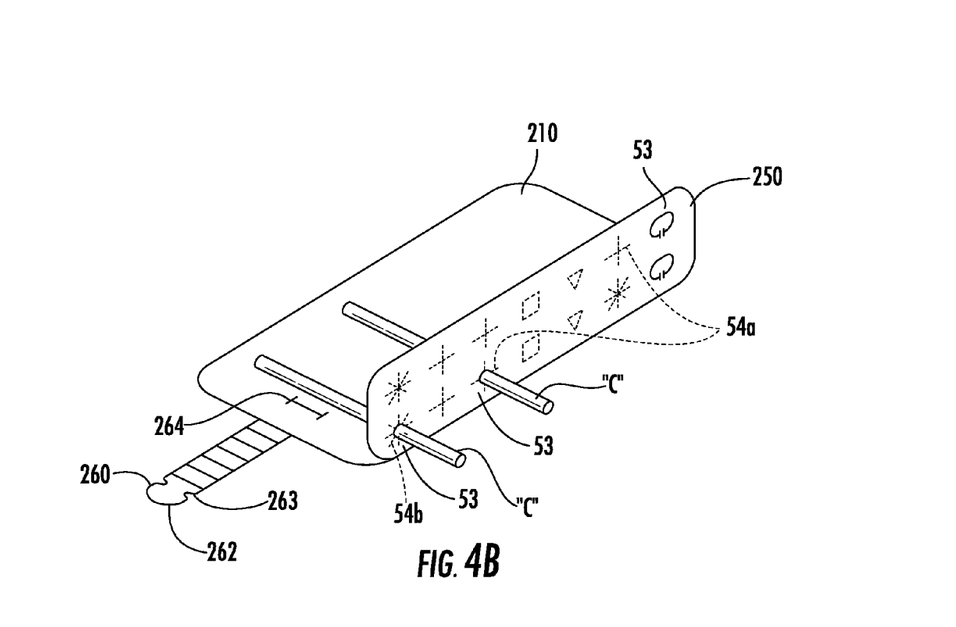
FIG. 4B is a front perspective view of the storage device of FIG. 4A, with the retaining member in the deployed configuration with the component disposed therein.
Figure 5:
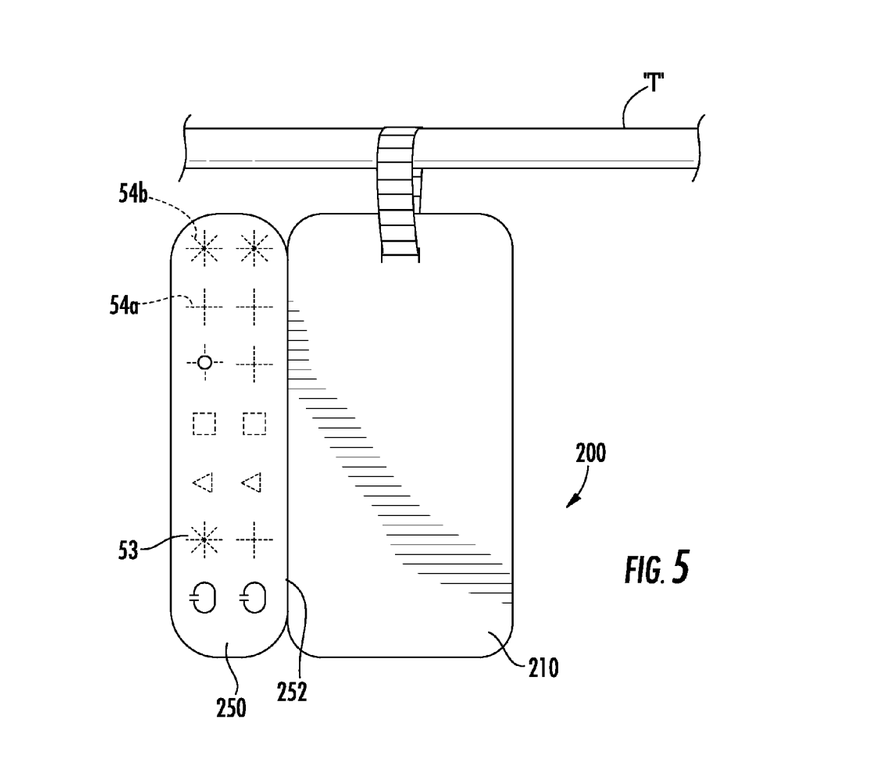
FIG. 5 is a top perspective view of the storage device of FIG. 4A with an attachment member and a tool.

With reference to FIGS. 4A-5, an alternate embodiment of a storage device is shown as storage device 200. Storage device 200 includes a receiving portion 210 and a retaining member 250 defining securing region 53 thereon. It should be appreciated that securing region 53 is common between storage devices 100 and 200, and further, that a plurality of securing regions 53 may be provided on retaining member 250. Each securing region 53 disposed on retaining member 250 may include a unique perforated configuration 54a-h, or alternatively, multiple securing regions 53 may share a particular perforated configuration 54a-h.

Retaining member 250 may be coupled to receiving portion 210 or may be monolithically formed therewith. It is envisioned that when transitioning between an initial configuration to a deployed configuration, retaining member 250 is bent, folded, or otherwise physically manipulated along crease 252. In the initial configuration, retaining member 250 is substantially planar with receiving portion 210 such that a low profile is maintained to promote compact and efficient packaging and storage within the operating theater. In the deployed configuration, retaining member 250 may be folded about crease 252 away from a plane defined by receiving portion 210 and into approximation therewith (FIG. 4B). It is envisioned that retaining member 250 may be maintained in the deployed configuration by any known means in the art, such as, for example, construction of storage device 200 from a deformable material, integration of a mechanical interlock mechanism between the retaining member 250 and receiving portion 210, such as a snap-fit, latch, or clasp, inclusion of an adhesive portion or strip disposed between the retaining member 250 and receiving portion 210, incorporation of a biasing member disposed between the retaining member 250 and receiving portion 210, construction of storage device 200 such that retaining member 250 is biased into the deployed configuration, or any combination thereof.

An attachment member 260 may extend from storage device 200 and serves to temporarily affix storage device 200 to the tool or component. Accordingly, storage device 200 may be temporarily affixed to, and/or packaged with, the tool or component when provided to the operator. In such an embodiment, storage device 200 is easily located by the operator when setting up the instrument or component for the procedure thus preventing storage device 200 from being misplaced or lost. Attachment member 260 may additionally be utilized to secure storage device 200 to a tray, table, or other location during the procedure, such that the location of storage device 200 is fixed within the operating theater.

Attachment member 260 may be flexible or partially-rigid and constructed from the same or differing materials as disclosed herein with respect to storage device 200. Attachment member 260 may further be monolithically formed with storage device 200 or may alternatively be coupled thereto by any known means in the art. Attachment member 260 may further come in a variety of forms, such as, for example, a suture, a tie-strap, a cable tie, an adhesive strip, a loop monolithically formed with storage device 200, a sleeve or sheath sized to slide over and receive a tool or component therein, a magnetic element adapted to adhere to a corresponding magnetic element of the tool or component, and/or any combination thereof. It is further envisioned that attachment member 260 may be disposed on, and/or extend from, any portion of storage device 200. With reference to FIGS. 4A-5, an exemplary embodiment of attachment member 260 is depicted as extending from receiving portion 210 of storage device 200. As illustrated in FIG. 5, attachment member 260 is configured such that after being looping or wrapping around a portion of the tool "T", a first end 262 which defines a notch 263 engages with a receiving slot 264 disposed on receiving portion 210, thereby temporarily affixing storage device 200 to tool "T". It should be appreciated that while attachment member 200 has been described and illustrated with respect to storage device 200, attachment member 260 may be utilized in a similar fashion with any of the storage devices disclosed herein.

Figure 6:
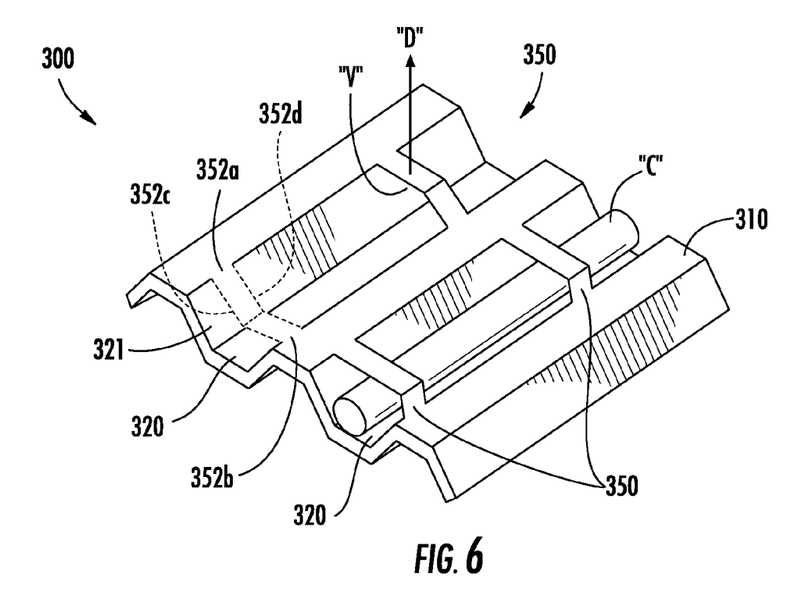
FIG. 6 is a front perspective view of a storage device in accordance with another embodiment of the present disclosure.

With reference to FIG. 6, a further embodiment of a storage device is shown as storage device 300. Storage device 300 includes a receiving portion 310, a plurality of receiving channels 320, and a plurality of retaining members 350. Each receiving channel 320 is configured to accommodate an individual tool or component and includes one or more retaining members 350 associated therewith. Each retaining member 350 has an initial configuration and a deployed configuration. In the initial configuration retaining member 350 is substantially flush with an inner surface 321 of receiving channel 320, and in the deployed configuration a void "V" is defined between the inner surface 321 of receiving channel 320 and an inner surface (not shown) of retaining member 350. Retaining member 350 may be transitioned from the initial configuration into the deployed configuration by pushing, pulling, or manipulating retaining member 350 in a direction away from receiving channel 320. It is contemplated that each retaining member 350 may be affixed on two sides 352a, 352b to receiving portion 310, while two sides 352c, 352d (shown in phantom) are perforated, or alternatively, may be completely severed from receiving portion 310. When transitioning retaining member 350 into the deployed configuration, retaining member 350 is moved away from the receiving channel 320 in the direction of arrow "D". Once in the deployed configuration, component "C" may slide along receiving channel 320 into the void "V" defined between receiving channel 320 and retaining member 350, thereby retaining component "C" therein. It is further contemplated that the inner surface of the retaining member 350, and/or the inner surface 321 of receiving channel 320, may be textured, and/or include a sticky or adhesive coating, such that the frictional securement of tools or components therein is increased.

Figures 7, 8:
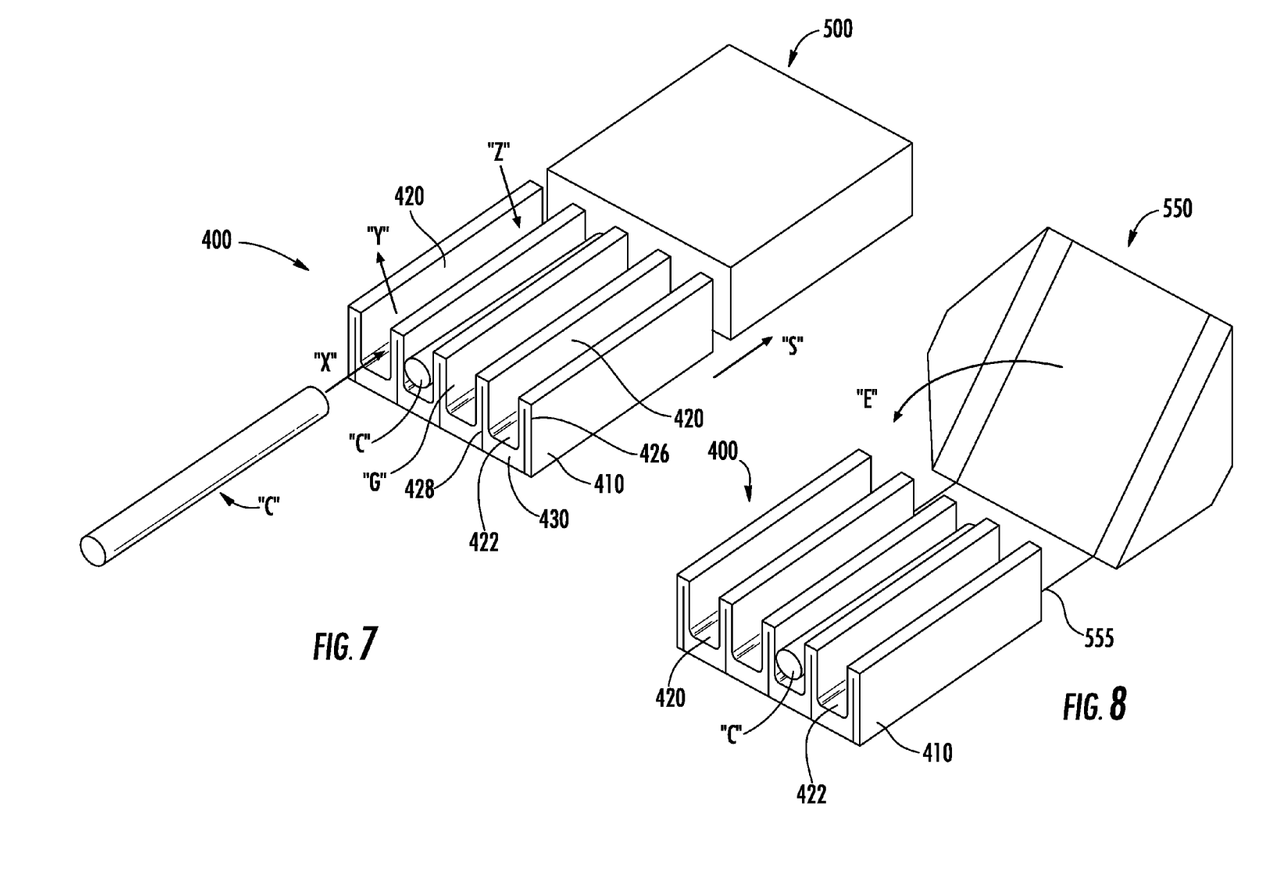
FIG. 7 is a front perspective view of a storage device in accordance with yet another embodiment of the present disclosure, with an embodiment of an enclosure.
FIG. 8 is a front perspective view of the storage device of FIG. 7 with another embodiment of an enclosure in accordance with the present disclosure.

With reference to FIG. 7, an alternate embodiment of a storage device is shown as storage device 400. Storage device 400 includes receiving portion 410 and a plurality of abutting receiving channels 420. Each receiving channel 420 is configured to receive an individual tool or component therein such that the tool or component is secured to storage device 400. Receiving channel 420 is defined by a set of arms 426, 428 extending away from a base 430 disposed on receiving portion 410. It is envisioned that an inner surface 422 of each receiving channel 420 may define a cross-sectional profile suited to complement a specific tool or component, or alternatively, the cross-sectional profile may be suited to accommodate a variety of tools or components. Further, the cross-sectional profile of receiving channel 420 may be generally arcuate, such that a generally "c" shape is defined. As illustrated in FIG. 7, a gap "G" is defined by receiving channel 420 which is large enough to permit component "C" to slide therein in the direction of arrow "X". It is contemplated that arms 426, 428 are configured to provide a snug fit, or tight tolerance, between the receiving channel 420 and the component "C", such that the component "C" is securely held therein. Arms 426, 428 may be further configured to accept component "C" from above, where component "C" is depressed in the direction of arrow "Z". Arms 426, 428 may be provide a biasing force, such that once component "C" is depressed from above, the arms 426, 428 inhibit component "C" from escaping from receiving channel 420 in the direction of arrow "Y". The configuration of the inner surface 422 and the set of arms 426, 426 defining receiving channel 420 provides frictional engagement with, and/or compressive forces upon, the outer surface of the tool or component inserted therein. It is further contemplated that the inner surface 422 of the receiving channel 420 may be textured, and/or include a sticky or adhesive coating, such that the frictional securement of tools or components therein is increased.

It is envisioned that storage device 400 may further include an enclosure 500 or an enclosure 550. Enclosures 500, 550 facilitate retention and affixation of used tools and components to receiving portion 410 of storage device 400. As illustrated in FIG. 7, receiving portion 410 may be slidably inserted into enclosure 500 along arrow "S", such that storage device 400 is thereby enclosed. With reference to FIG. 8, enclosure 550 extends from a portion of receiving portion 410 and is foldable along edge 555 in the direction of arrow "E", such that storage device 400 may be enclosed. It should be appreciated that while enclosures 500, 550 have been described and illustrated with respect to storage device 400, enclosures 500, 550 may be utilized in a similar fashion with any of the storage devices disclosed herein.

It is further contemplated that receiving portions 10, 210, 310, and 410 of storage devices 100, 200, 300, and 400, respectively, may include one or more visual indicia disposed thereon to facilitate the accounting of tools or components used during the procedure. Visual indicia may include, for example, textural or color coded indicators, sequential punch holes, a section intended for operators to transcribe notes or comments thereon, or any combination thereof.

Storage devices 100, 200, 300, and 400 may be constructed from any suitable material to provide rigid support while also permitting storage devices 100, 200, 300, and 400 to transition into any of the configurations as described herein. Storage devices 100, 200, 300, and 400 may be made in whole, or in part, from a variety of materials, such as, for example, paper, pressed paper, cardboard, polymers, metals, metal alloys, or any combination thereof. It is contemplated that storage devices 100, 200, 300, and 400 may be further adapted to withstand sterilization through any known means in the art, such as, for example, steam sterilization, flash sterilization, ethylene oxide sterilization, or hydrogen peroxide gas plasma sterilization.

It is further envisioned that storage devices 100, 200, 300, and 400 may be made in whole, or in part, from absorbent materials, such as, for example, water-absorbing polymers or fiber-based products, and/or may include an absorbent coating thereon. Providing storage devices 100, 200, 300, and 400 with an absorbent element facilitates the collection and retention of biological material or waste which may be deposited thereon as a result of contact with used tools or components. It is envisioned that a used component may contain residual biological material or waste, such as blood, which may contaminate the surgical theater if permitted to freely come into contact with surrounding structures, tools, personnel, etc. With an absorbent element, storage devices 100, 200, 300, and 400 may thus facilitate a clean and sterile environment by absorbing such waste. It is further envisioned that storage devices 100, 200, 300, and 400 may contain absorbent portions configured to absorb biological material or waste and impermeable portions configured to resists the absorbance of liquids. In such a configuration, the cost of materials during manufacturing may be reduced, structural rigidity may be increased, unit weight may be reduced, packaging size and cost may be reduced, and/or any combination of the above.

With reference to FIGS. 1A-6, a method of using a storage device will now be described with reference to storage device 100. It should be appreciated that storage device 100 is substantially similar to storage devices 200 and 300. Thus, for the sake of brevity, the method of using storage device 100 will be described herein.

In use, storage device 100 is provided to an operator with retaining member 50 in the initial configuration. It is envisioned that a tool or component may be provided, such that storage device 100 is temporarily fixed to the tool or component. Storage device 100 may be provided in a sterilized package, independent of or together with, a sterilized tool or component, such that storage device 100 and the tool or component may be sterilized in a common packaging. With the storage device 100 removed from the packaging, and/or disconnected from the tool or component, retaining member 50 may be transitioned into the deployed configuration. It is envisioned that storage device 100 may be affixed to a specific location within the operating theater, such that movement of storage device 100 is inhibited. Storage device 100 is now ready to receive and affix the tool or component, or a plurality of tools or components, thereto.

As tools or components are unpacked, used, depleted, and/or replaced, the tool or component may be affixed to storage device 100, such that the operator may accurately account for the number of tools or components utilized during the procedure. For example, in a situation where the operator is aware that five staple cartridges were unpackaged and used during the procedure, five depleted staple cartridges should be affixed to storage device 100. Storage device 100 permits the operator to accurately compare the quantity of unpacked tools or components to the quantity of tools or components retained on storage device 100, and thus more confidently assess if a tool or component is unaccounted for.

With regard to storage devices 100 and 200, to affix component "C" to storage device 100, an end of the component "C" is put into abutment to securing region 53, such that the component "C" is insertable therethrough (FIGS. 3A, 3B, and 4B). With regard to storage device 300, the component "C" is slid in receiving channel 320 between receiving channel 320 and retaining member 350 (FIG. 6).

Component "C" is thereby secured to storage devices 100, 200, or 300, providing the operator a means to account for the discarded component throughout the procedure.

With reference to FIGS. 7 and 8, a method of using storage device 400 will now be described. Storage device 400 may be provided in a sterilized package, independent of or together with, a sterilized tool or component, such that storage device 400 and the tool or component may be sterilized in a common packaging. Storage device 400 may further be temporarily affixed to the tool or component. With the storage device 400 removed from the packaging, and/or disconnected from the tool or component, storage device 400 may be positioned at, and/or affixed to, a desirable location within the operating theater. Storage device 400 is now ready to receive a tool or component within receiving channels 420. To affix a component "C" to storage device 400, component "C" is slid in the direction of arrow "X", and/or depressed in the direction of arrow "Z", into gap "G" of receiving channel 420 (FIG. 7). Component "C" is thereby secured to storage device 400 providing the operator a means to account for the discarded component through the procedure. Storage device 400 may be enclosed by enclosures 500 or 550 to further secure the component "C" and/or any biological waste thereon.

A kit for storing a medical component in the operating theater using a storage device will now be discussed with reference to FIGS. 1A-8. The kit may include at least one storage device 100. It is envisioned that storage device 100 is provided with the retaining member 50 in the initial configuration. It is further envisioned that the kit may include a tool or component in a common package with storage device 100, such that storage device 100 is tethered or temporarily fixed to the tool or component. Storage device 100 may be provided in a sterile packaging, with or without, a sterilized tool or component therein. It should be appreciated that the kit may alternatively, or additionally, include storage devices 200, 300, or 400, or a plurality of storage devices 200, 300, or 400.

Although embodiments have been described in detail with reference to the accompanying drawings for the purpose of illustration and description, it is to be understood that the inventive processes and apparatus are not to be construed as limited thereby. It will be apparent to those of ordinary skill in the art that various modifications to the foregoing embodiments may be made without departing from the scope of the disclosure.

The invention claimed is:

1. A storage device comprising:
 a receiving portion adapted to support a medical component thereon, the receiving portion including an absorbent coating; and
 a retaining member coupled to the receiving portion and transitionable between an initial configuration and a deployed configuration, the retaining member defining at least one securing region thereon, wherein the at least one securing region is circumscribed by material of the retaining member, wherein a portion of the retaining member is spaced away from a plane defined by a surface of the receiving portion in the deployed configuration thereby defining an opening through the receiving portion, a surface of the retaining member defining an acute angle relative to the plane in the deployed configuration, and the at least one securing region of the retaining member is configured to receive the medical component therein.

2. The storage device of claim 1, wherein the retaining member and the surface of the receiving portion are coplanar in the initial configuration.

3. The storage device of claim 1, wherein the receiving portion further includes a raised lip extending along an outer perimeter thereof.

4. The storage device of claim 1, wherein the at least one securing region has a perforated pattern.

5. The storage device of claim 1, further comprising an attachment member including a first end and a second end, the attachment member coupled at the first end to the receiving portion, and the receiving portion includes a receiving slot disposed thereon, the second end of the attachment member configured to temporarily affix to the receiving slot of the receiving portion.

6. The storage device of claim 1, further comprising a plurality of retaining members, wherein each retaining member of the plurality of retaining members is independently transitionable between the initial and deployed configurations.

7. The storage device of claim 1, wherein the receiving portion further includes a perimeter configured to increase frictional resistance thereon, such that the medical component is frictionally inhibited from escaping the receiving portion.

8. The storage device of claim 1, wherein the retaining member includes a deformable material configured to be temporarily fixed in the initial configuration and biased into the deployed configuration, such that once the retaining member is released from the initial configuration the retaining member assumes the deployed configuration.

9. The storage device of claim 1, wherein the at least one securing region of the retaining member is configured to receive a medical component selected from the group consisting of: a reloadable staple cartridge, a reloadable tack cartridge, a removable end effector, and a surgical mesh.

10. A storage device comprising:
 a receiving portion including a receiving slot and an absorbent material thereon, the receiving portion adapted to support a medical component thereon;
 a retaining member coupled to the receiving portion and transitionable between an initial configuration and a deployed configuration, the retaining member defining a plurality of securing regions thereon; and
 an attachment member including a first end and a second end, the first end coupled to the receiving portion and the second end is configured to temporarily affix to the receiving slot of the receiving portion,
 wherein the retaining member is coplanar with the receiving portion in the initial configuration, and the retaining member is spaced away from a plane defined by a surface of the receiving portion in the deployed configuration, and
 wherein the medical component is insertable through each securing region of the plurality of securing regions of the retaining member, each securing region of the plurality of securing regions configured to exert a compressive force upon an outer surface of the medical component thereby securing the medical component therein.

11. A kit comprising:
 a storage device including:
  a receiving portion including an absorbent coating; and
  a retaining member coupled to the receiving portion and transitionable between an initial configuration and a deployed configuration, the retaining member defining a securing region thereon, wherein the securing region is defined by a contiguous outer surface, a portion of the retaining member spaced away from a plane defined by a surface of the receiving portion in the deployed configuration thereby defining an opening through the receiving portion, a surface of the retaining member defining an acute angle relative to the plane in the deployed configuration; and a medical component insertable into the securing region.

12. The kit of claim 11, further comprising a medical tool.

13. The kit of claim 12, wherein the medical tool is selected from the group consisting of: a surgical stapler, a surgical tack applier, a reloadable fixation device, a vessel sealer, an ablation probe, an endoscopic instrument, and a retractor.

14. The kit of claim 11, wherein the medical component is selected from the group consisting of: a reloadable staple cartridge, a reloadable tack cartridge, a removable end effector, and a surgical mesh.

15. The kit of claim 12, wherein the storage device further includes an attachment member including a first end and a second end, the attachment member coupled at the first end to the receiving portion, and the receiving portion includes a receiving slot disposed thereon, the second end of the attachment member configured to temporarily affix to the receiving slot of the receiving portion, and wherein the attachment member temporarily secures the storage device to the medical component or the tool.

16. A method of storing a medical tool or component comprising:

transitioning a retaining member of a storage device from an initial configuration into a deployed configuration, such that a portion of the retaining member is spaced away from a plane defined by a surface of a receiving portion of the storage device thereby defining an opening through the receiving portion, a surface of the retaining member defining an acute angle relative to the plane in the deployed configuration and the receiving portion including an absorbent coating;

approximating a medical component to a securing region of the retaining member, the securing region defining a perforated pattern thereon; and inserting the medical component through the securing region and through a thickness of the retaining member, such that the medical component is affixed thereto and is disposed adjacent the absorbent area.

17. The method of claim 16, further comprising separating the storage device from a medical tool, the storage device attached to the medical tool with an attachment member.

18. The method of claim 16, further comprising providing the storage device in the initial configuration, wherein the retaining member and the receiving portion are coplanar in the initial configuration.

19. The storage device of claim 10, wherein the absorbent material is a coating.

* * * * *